United States Patent [19]

Kollmeyer

[11] 4,053,622

[45] Oct. 11, 1977

[54] PHENYL ESTERS OF 3-METHYL-2-(1-NITRO-2-OXO-2-PHENOX-YETHYLIDENE)-1-IMIDAZOLIDINECAR-BOXYLIC ACIDS

[75] Inventor: Willy D. Kollmeyer, Modesto, Calif.

[73] Assignee: Shell Oil Company, Houston, Tex.

[21] Appl. No.: 759,596

[22] Filed: Jan. 14, 1977

[51] Int. Cl.$^2$ .................. A61K 31/415; C07D 233/40
[52] U.S. Cl. ................................. 424/273 R; 548/342
[58] Field of Search .................. 260/309.7; 424/273

[56] References Cited

U.S. PATENT DOCUMENTS 3,948,934  4/1976  Tieman et al. .................. 260/309.7

OTHER PUBLICATIONS

Meyer et al., Chem. Abst., 1973, vol. 79, No. 146519d.
Wennerbeck, Acta Chem. Scand., 1973, vol. 27, pp. 258–270.

*Primary Examiner*—Natalie Trousof

[57] ABSTRACT

Insecticidal phenyl esters of 3-methyl-2-(1-nitro-2-oxo-2-phenoxyethylidene)-1-imidazolidinecarboxylic acids.

3 Claims, No Drawings

PHENYL ESTERS OF 3-METHYL-2-(1-NITRO-2-OXO-2-PHENOXYETHYLIDENE)-1-IMIDAZOLIDINECARBOXYLIC ACIDS

DESCRIPTION OF THE INVENTION

It has been found that useful insecticidal activity is possessed by phenyl esters of 3-methyl-2-(nitro-2-oxo-2-phenoxyethylidene) -1-imidazolidinecarboxylic acids. These compounds are described by the formula:

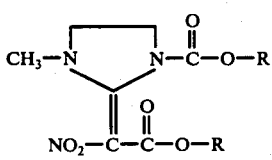

(I)

wherein both of R are the same and are phenyl or phenyl substituted from one to three halogen atoms or by one of nitro, cyano, alkyl, mono- and poly-haloalkyl, alkoxy, alkylthio, alkylsulfinyl, alkylsulfonyl and alkanoyl, wherein the alkyl moiety contains from one to six carbon atoms. By halogen is meant chlorine, bromine, iodine and fluorine — bromine, chlorine and fluorine being preferred. Suitably, any alkyl moiety is of straight-chain or branched-chain configuration; methyl is preferred.

For illustration, preparation of typical individual species of the genus are described in the examples included hereinafter. Other typical, illustrative species of this genus include those wherein R is phenyl substituted by
4-trifluoromethyl
4-methylthio
4-methylsulfinyl
4-methylsufinyl
4-nitro
2-chloro
2-methyl
2,4-dichloro
2,4,5-trichloro Compounds of the invention can be prepared by treating the appropriate 1-methyl-3-(R-oxycarbonyl-)imidazolium chloride with an equimolar amount of 1-methyl-2-(nitromethylene) imidazolidine (U.S. Pat. No. 3,948,934).

The imidazolium chloride can be prepared by treating 1-methylimidazole with an equimolar quantity of the R-chloro-formate, preferably in a suitable solvent and at a low temperature, for example, about 0°–5° C. A suitable general method for conducting this procedure comprises adding a solution of the acid cholride in methylene chloride slowly (e.g., dropwise) to a cold (e.g., 0°–5° C) solution of the N-methylimidazole in the same solvent, stirring the cold mixture for a period of from about 15 minutes to one hour to ensure essentially complete reaction.

Some of the R-chloroformates are known compounds: Oesper et. al., J. Am. Chem. Soc., 47, 2609 (1925); also Chemical Abstracts, 82, 138788n (1975); 82, 111249a (1975); 83, P43188 (1975). Others can be prepared by treating the appropriate phenol with phosgene in ether solution in the presence of N, N-dimethylaniline according to the method of Oesper et al, supra.

The 1-methyl-2-(nitromethylene) imidazolidine (a solid) is then added slowly to the stirred solution of the imidazolium chloride, at the low temperature, then the mixture is warmed to or somewhat above room temperature and stirred at that temperature until the reaction is complete.

The desired product can be isolated from the crude reaction mixture and purified by conventional methods, such as filtration, extraction, crystallization and these procedures for preparing compounds of this invention are illustrated in the following examples of the preparation of particular species of such compounds. In all cases, the identity of the product, and of any intermediate employed, was confirmed by appropriate chemical and spectral analyses.

EXAMPLE 1 -
(3-methyl-2-(1-nitro-2-oxo-2-phenoxyethylidene)-1-imidazolidine carboxylic acid phenyl ester     (1)

A solution of 15.66 g of phenyl chloroformate in 25 ml of methylene chloride was added to a stirred and ice-cooled solution of 8.21 g of 1-methylimidazole in 175 ml of methylene chloride. To the resulting white suspension was added 7.15 g of 1-methyl-2-(nitromethylene) imidazolidine in portions as a solid. After stirring overnight at room temperature, the reaction mixture was washed twice with water. The organic layer was dried (MgS0$_4$) and concentrated. The residual orange syrup was treated with water, and this mixture allowed to stand at room temperature overnight. The resulting solid was isolated by filtration. Trituration with ethyl acetate gave white powder. Recrystallization from a mixture of 60 ml of dimethyl sulfoxide and 45 ml of water gave (1), as a white solid, m.p.: 214°–215° C.

EXAMPLES 2–7.

In a similar manner, the following further esters were prepared:

| Compound | R | melting point (° Cl) |
|---|---|---|
| 2 | 4-Cl— | 197–200[1] |
| 3 | 4-CH$_3$— | 190–193[1] |
| 4 | 4-CN— | 202–203[1] |
| 5 | 4-CH$_3$—O— | 142–144[1] |
| 6 | 4-CH$_3$—C(=O)— | 120–124[1] |
| 7 | 3,4-Cl$_2$— | 204[1] |

[1]melts with decomposition

Compounds of this invention exhibit useful insecticidal activity, being of particular interest for control of the larvae "caterpillar" or "worm" forms of insects of the genus Heliothis, such as H. zea (corn earworm, cottom bollworm, tomato fruitworm), H. virescens (tobacco budworm); the genus Agrotis, such as A. ipsilon (black cutworm); the genus Trichoplusia, such as T. ni (cabbage looper), and the genus Spodoptera, such as S. littoralis (Egyptian cotton leafworm). In tests that have been conducted they have exhibited low, or no, toxicity to other insects such as aphids, houseflies, the 2-spotted spider mite and mosquito larva.

Activity of compounds of this invention with respect to insects was determined by using standardized tests to establish the LC$_{50}$ dosage (in milligrams of test compound per 100 milliliters of solvent or liquid carrier required in the solution or suspension of test compound used) to kill 50% of the test insects. The test insects were the housefly, corn earworm, pea aphid and 2-spotted spider mite. Activity with respect to mosquito larvae was determined by placing the larvae in water containing the test compound.

All of compounds 1 through 7 were found to be active with respect to the corn earworm. Compounds 2, 4 and 7 were slightly active with respect to the mosquito larvae. None of the compounds was active with respect to the other species of insects.

The invention includes within its scope insecticidal compositions comprising an adjuvant — that is, a carrier, optionally a surface-active agent — and, as active ingredient, at least one insecticide of this invention. Likewise the invention includes also a method of combatting insect pests at a locus which comprises applying to the locus an effective amount of at least one insecticide of the invention.

The term "carrier" as used herein means a material which may be inorganic or organic and of synthetic or natural origin, with which the active compound is mixed or formulated to facilitate its applications to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates, elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example, superphosphates.

Suitable liquid carriers include solvents for the compounds of this invention and liquids in which the toxicant is insoluble or only slightly soluble.

Examples of such solvents and liquid carriers generally are alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions such as kerosene, light mineral oils, chlorinated hydrocarbons, such as carbon tetrachloride, perchlorethylene, trichloroethane, including liquefied normally vaporous gaseous compounds. Mixtures of different liquids are often suitable.

If used, the surface-active agent may be an emulsifying agent or a dispersing agent or a wetting agent. It may be nonionic or ionic. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acid salts of low molecular weight, mono-, di- and trialkylamines; condensates of these with ethylene oxide and/or propylene oxide; condensation products of fatty alcohols or alkyl phenols for example, p-octylphenol or p-octylcresol, with ethylene oxide and/or propylene oxide; sulfates or sulfonates of these condensation products of fatty alcohols or alkyl phenols for example, p-octylphenol or p-octylcresol, with ethylene oxide and/or propylene oxide; sulfates or sulfonates of these condensation products; alkali or alkaline earth metal salts, preferably sodium salts, of sulfuric or sulfonic acids esters containing at least 10 carbon atomis in the molecule, for example, sodium lauryl sulfate, sodium secondary alkyl sulfates, sodium salts of sulfonated castor oil, and sodium alkylaryl sulfonates such as sodium dodecyclbenzene sulfonate; and polymers of ethylene oxide and copolymers of ethylene oxide and propylene oxide.

The compositions of the invention may be formulated as wettable powders, dusts, granules, solutions, emulsifiable concentrations, emulsions, suspension concentrates or aerosols. Encapsulated formulations and controlled release formulations also are contemplated, as are bait formulations. Wettable powders are usually compounded to contain 25, 50 or 75% of toxicant and usually contain, in addition to solid carrier, 3–10%w of a dispersing agent and, where necessary, up to 10%w of stabilizer(s) and/or other additives such as penetrants or stickers. Dusts are usually formulated as a dust concentrate having a similar composition to that of a wettable powder but without a dispersant, and are diluted in the field with further solid carrier to give a composition usually containing ½–10%w of toxicant. Granules may be manufactured by agglomeration or impregnation techniques. Generally, granules will contain ½–25%w toxicant and 0–10%w of additives such as stabilizers, slow release modifiers and binding agents. Emulsifiable concentrates usually contain, in addition to the solvent, and when necessary, co-solvent, 10–50%w/v toxicant, 2–20%w/v emulsifiers and 0–20%w/v of appropriate additives such as stabilizers, penetrants and corrosion inhibitors. Suspension concentrates are compounded so as to obtain a stable, non-sedimenting, flowable product and usually contain 10–75%w toxicant, 0–5%w of dispersing agents, 0.1–10%w of suspending agents such as protective colloids and thixotropic agents, 0–10%w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention may also contain other ingredients, for example, other compounds possessing pesticideal, herbicidal or fungicidal properties, or attractants, such as pheromones, attractive food ingredients, and the like, for use in baits and trap formulations.

These compositions are applied in sufficient amount to supply the effective dosage of toxicant at the locus to be protected. Thus dosage is dependent upon many factors, including the carrier employed, the method and conditions of application, whether the formulation is present at the locus in the form of an aerosol, or as a film, or as discrete particles, the thickness of film or size of particles, the insect species to be controlled and the like, proper consideration and resolution of these factors to provide the necessary dosage of active material at the locus being within the skill of those versed in the art. In general, howeve, the effective dosage of toxicants of this invention at the locus to be protected — i.e. the dosage to which the insect contacts — is of the order of 0.001% to 0.5% based on the total weight of the formulation, though under some circumstances the effective concentration will be as little as 0.0001% or as much as 2%, on the same basis.

I claim:

1. A compound of the formula:

(I)

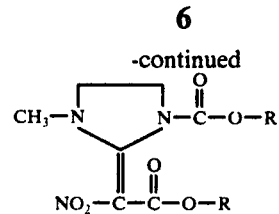

wherein both of R are the same and are phenyl or phenyl substituted by from one to three halogen atoms or by one of nitro, cyano, alkyl, mono- and polyhaloalkyl, alkoxy, alkylthio, alkylsulfinyl, alkylsulfonyl and alkanoyl, wherein the alkyl moiety contains from one to six carbon atoms.

2. An insecticidal composition comprising an insecticidally effective amount of a compound of claim 1 together with an adjuvant therefore.

3. A method for killing insects which comprises contacting them with a lethal dosage of a compound of claim 1.